(12) United States Patent
Song et al.

(10) Patent No.: US 10,548,674 B2
(45) Date of Patent: Feb. 4, 2020

(54) ROBOTIC GUIDE FOR MEDICAL DEVICE

(71) Applicant: YellowDot Innovations, LLC, Windermere, FL (US)

(72) Inventors: Sang-Eun Song, Orlando, FL (US); Jeremy Burt, Windermere, FL (US)

(73) Assignee: YELLOWDOT INNOVATIONS, LLC, Windermere, FL (US)

( * ) Notice: Subject to any disclaimer, the term of this patent is extended or adjusted under 35 U.S.C. 154(b) by 270 days.

(21) Appl. No.: 15/642,953

(22) Filed: Jul. 6, 2017

(65) Prior Publication Data

US 2019/0008594 A1     Jan. 10, 2019

(51) Int. Cl.
| | | |
|---|---|---|
| *A61B 34/30* | (2016.01) | |
| *A61B 90/11* | (2016.01) | |
| *A61B 17/34* | (2006.01) | |
| *A61B 90/50* | (2016.01) | |
| *A61B 90/57* | (2016.01) | |

(52) U.S. Cl.
CPC .......... *A61B 34/30* (2016.02); *A61B 17/3403* (2013.01); *A61B 90/11* (2016.02); *A61B 90/50* (2016.02); *A61B 2017/3409* (2013.01); *A61B 2034/302* (2016.02); *A61B 2090/508* (2016.02); *A61B 2090/571* (2016.02)

(58) Field of Classification Search
CPC ........ A61B 34/30–35; A61B 2034/301; A61B 90/11; A61B 90/10–2090/103; A61B 90/13; A61B 17/3403–2017/3411; A61B 10/0233–0283
USPC ................................................. 606/417, 429
See application file for complete search history.

(56) References Cited

U.S. PATENT DOCUMENTS

| | | | | |
|---|---|---|---|---|
| 4,602,622 A | * | 7/1986 | Bar .......................... | A61B 6/02 606/130 |
| 4,608,977 A | * | 9/1986 | Brown ................... | A61B 90/11 378/162 |
| 4,805,615 A | * | 2/1989 | Carol ..................... | A61B 90/11 403/115 |
| 4,911,173 A | * | 3/1990 | Terwilliger ............. | A61B 8/12 600/101 |

(Continued)

OTHER PUBLICATIONS

Johns Hopkins Medicine, URobotics Brady Urological Institute, "MrBot: The first fully-actuated MRI robot," Copyright The Johns Hopkins University, The Johns Hopkins Hospital, and Johns Hopkins Health System, <http://urobotics.urologyjhu.edu/projects/MrBot/>, Downloaded from internet Jul. 5, 2017.

(Continued)

*Primary Examiner* — Katrina M Stransky
*Assistant Examiner* — Brigid K Byrd
(74) *Attorney, Agent, or Firm* — Fox Rothschild LLP; Robert J. Sacco

(57) ABSTRACT

Robotic guide for slender elongated medical device (SEMD) includes first and a second guide mechanisms, each including a pair of adjacent control plates. First and second transverse guide slots defined in pairs of adjacent control plates control a position of an SEMD guide having a spherical outer bearing surface. The guide position is controlled by selectively varying a relative position of the adjacent control plates, whereby robotic control is obtained over both a lateral displacement of an SEMD axis and an insertion angle of an SEMD alignment axis.

20 Claims, 13 Drawing Sheets

(56) References Cited

U.S. PATENT DOCUMENTS

| | | | | |
|---|---|---|---|---|
| 5,201,742 | A * | 4/1993 | Hasson | A61B 17/3403 606/1 |
| 5,263,956 | A * | 11/1993 | Nobles | A61B 90/11 606/1 |
| 5,702,405 | A * | 12/1997 | Heywang-Koebrunner | A61B 5/0555 600/411 |
| 5,943,719 | A * | 8/1999 | Feldman | A61B 17/3403 606/130 |
| 6,398,711 | B1 * | 6/2002 | Green | A61M 25/01 600/7 |
| 10,321,963 | B2 * | 6/2019 | Comber | A61B 34/30 |
| 2001/0004676 | A1 * | 6/2001 | Ouchi | A61B 1/00133 600/106 |
| 2002/0156365 | A1 * | 10/2002 | Tsekos | A61B 5/0555 600/411 |
| 2003/0036766 | A1 * | 2/2003 | Engelhard | A61B 90/11 606/130 |
| 2005/0182317 | A1 * | 8/2005 | Haddad | A61B 17/17 600/424 |
| 2005/0267373 | A1 * | 12/2005 | Lee | A61B 8/0833 600/471 |
| 2006/0069383 | A1 * | 3/2006 | Bogaerts | A61B 17/3403 606/1 |
| 2006/0184063 | A1 * | 8/2006 | Miller | A61B 10/0266 600/568 |
| 2006/0270902 | A1 * | 11/2006 | Igarashi | A61B 17/3403 600/114 |
| 2008/0071215 | A1 * | 3/2008 | Woods | A61B 17/3403 604/116 |
| 2008/0306375 | A1 * | 12/2008 | Sayler | A61B 5/055 600/417 |
| 2011/0009879 | A1 * | 1/2011 | Derrick | A61B 17/3403 606/130 |
| 2011/0028791 | A1 * | 2/2011 | Marino | A61B 17/3421 600/203 |
| 2012/0253383 | A1 * | 10/2012 | Russo | A61B 17/3423 606/201 |
| 2012/0316575 | A1 * | 12/2012 | Farin | A61B 17/00234 606/130 |
| 2013/0053959 | A1 * | 2/2013 | Lizardi | A61B 17/1714 623/13.14 |
| 2013/0116546 | A1 * | 5/2013 | Requardt | A61B 5/055 600/414 |
| 2013/0123802 | A1 * | 5/2013 | Comber | A61B 34/30 606/130 |
| 2013/0165941 | A1 * | 6/2013 | Murphy | A61B 17/8897 606/91 |
| 2013/0289399 | A1 * | 10/2013 | Choi | A61B 17/1671 600/431 |
| 2014/0018822 | A1 * | 1/2014 | Main | A61B 17/3403 606/130 |
| 2014/0276202 | A1 * | 9/2014 | Polster | A61B 10/0266 600/564 |
| 2014/0276876 | A1 * | 9/2014 | Arthur | A61B 17/8805 606/93 |
| 2014/0330277 | A1 * | 11/2014 | Ogrodnik | A61B 17/1703 606/87 |
| 2014/0350572 | A1 * | 11/2014 | Elhawary | A61B 90/11 606/130 |
| 2015/0090057 | A1 * | 4/2015 | Pacheco | A61M 25/0113 74/25 |
| 2015/0094653 | A1 * | 4/2015 | Pacheco | A61M 25/0113 604/95.01 |
| 2015/0202011 | A1 * | 7/2015 | Gowda | A61B 17/3423 606/130 |
| 2016/0030130 | A1 * | 2/2016 | Tahmasebi Maraghoosh | A61N 5/1027 600/424 |
| 2017/0020623 | A1 * | 1/2017 | Glossop | A61B 90/11 |
| 2017/0181766 | A1 * | 6/2017 | Damar | A61B 17/32053 |
| 2017/0196590 | A1 * | 7/2017 | Sperry | A61B 17/3403 |
| 2017/0265890 | A1 * | 9/2017 | Page | A61B 17/3417 |
| 2017/0333724 | A1 * | 11/2017 | Lee | A61N 2/006 |

OTHER PUBLICATIONS

CiiS Lab, Johns Hopkins University, "MRI Compatible Robotics," Laboratory for Computational Sensing Robotics, research.mri_compatible_robotics.txt, Last modified Jul. 7, 2014, <https://ciis.lcsr.jhu.edu/dokuwiki/doku.php? d=research.mri_compatible_robotics>, Downloaded from internet Jul. 5, 2017.

UMC Utrecht, "Brachytherapy prostate, Implant Technique for MRI Guided Prostate Brachytherapy," copyright 2017 Universitair Medisch Centrum Utrecht, <http://www.umcutrecht.nl/en/Research/Research-centers/UMC-Utrecht-Center-for-Image-Sciences/Research-programs/MR-Radiotherapy/MRI-guided-Radiotherapy/Brachytherapy-prostate>, Downloaded from internet Jul. 5, 2017.

Kapoor, A., et al., "MRI compatible Hands-on Cooperative Control of a Pneumatically Actuated Robot," IEEE Int. Conf Robot Autom., Jul. 6, 2009, 2009, 2681-2686, doi: 10.1109/ROBOT.2009.5152541.

The Perk Lab, Laboratory for Percutaneous Surgery, "Robot-assisted prostate brachytherapy," <http://perk.cs.queensu_ca/contents/robotassisted-prostate-brachytherapy>, Downloaded from internet Jul. 5, 2017.

Engineering Services, Inc., "Medical Robots," Copyright Engineering Services, Inc., 2017, <http://esit.com/index.php/read-more/155-medical-robots-s>, Downloaded from internet Jul. 5, 2017.

Su, H., et al., "Piezoelectrically Actuated Robotic System for MRI-Guided Prostate Percutaneous Therapy," Nov. 5, 2014, DOI: 10.1109/TMECH2014.2359413.

* cited by examiner

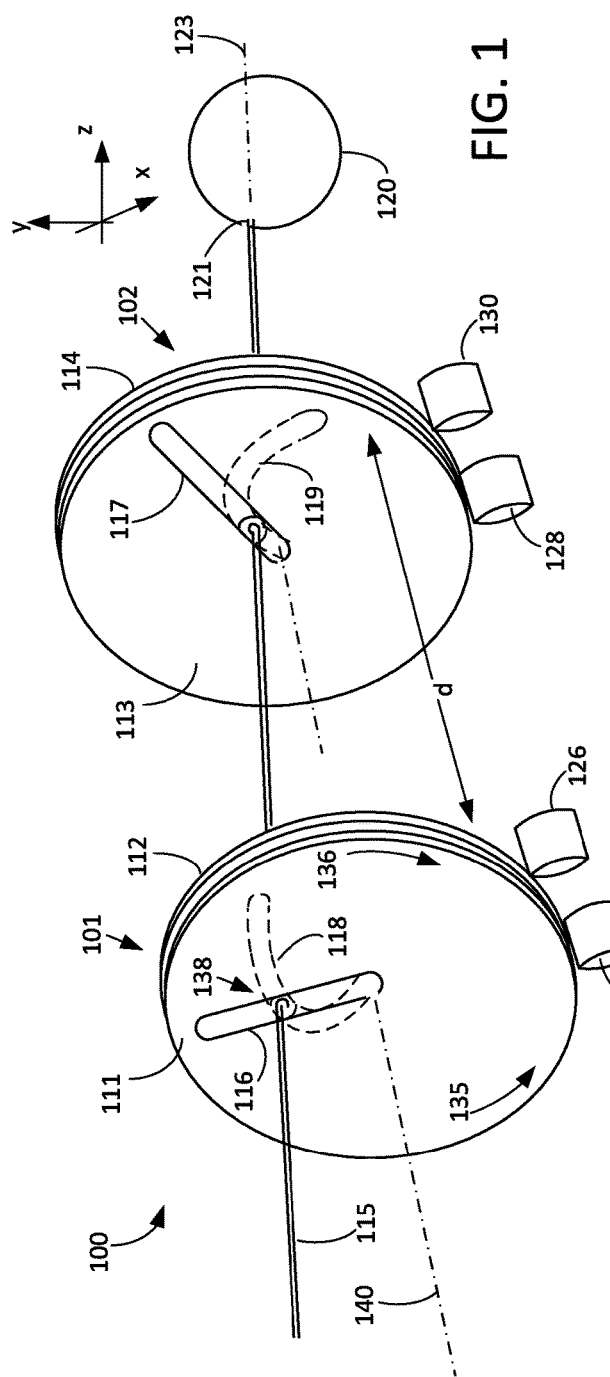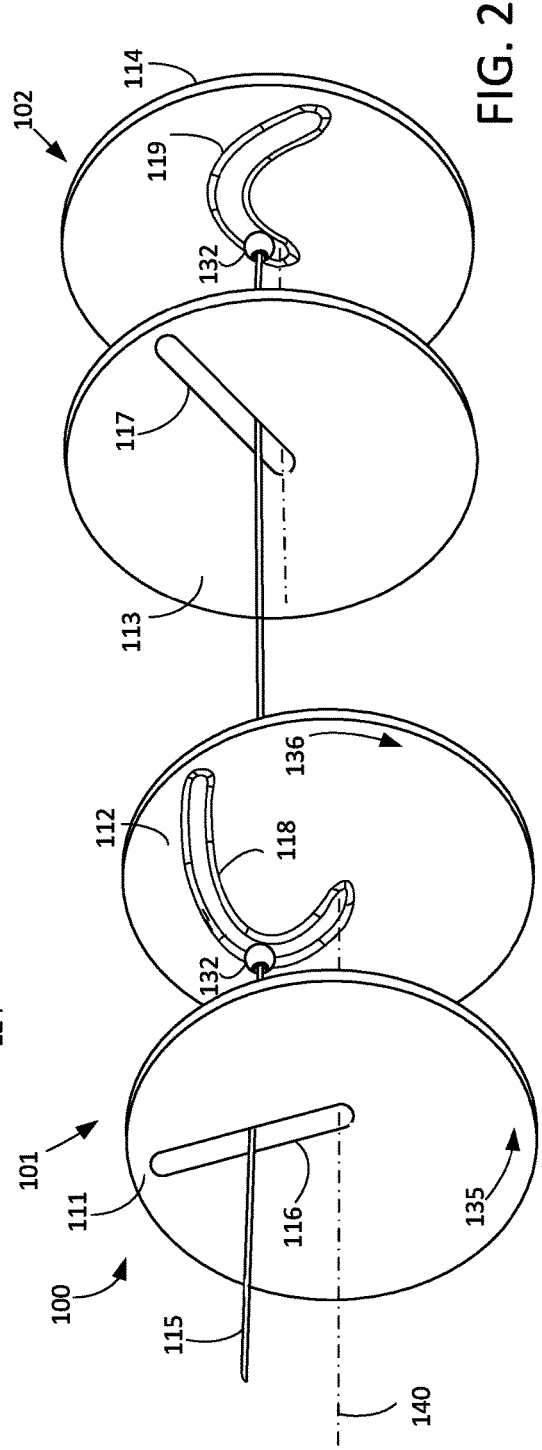

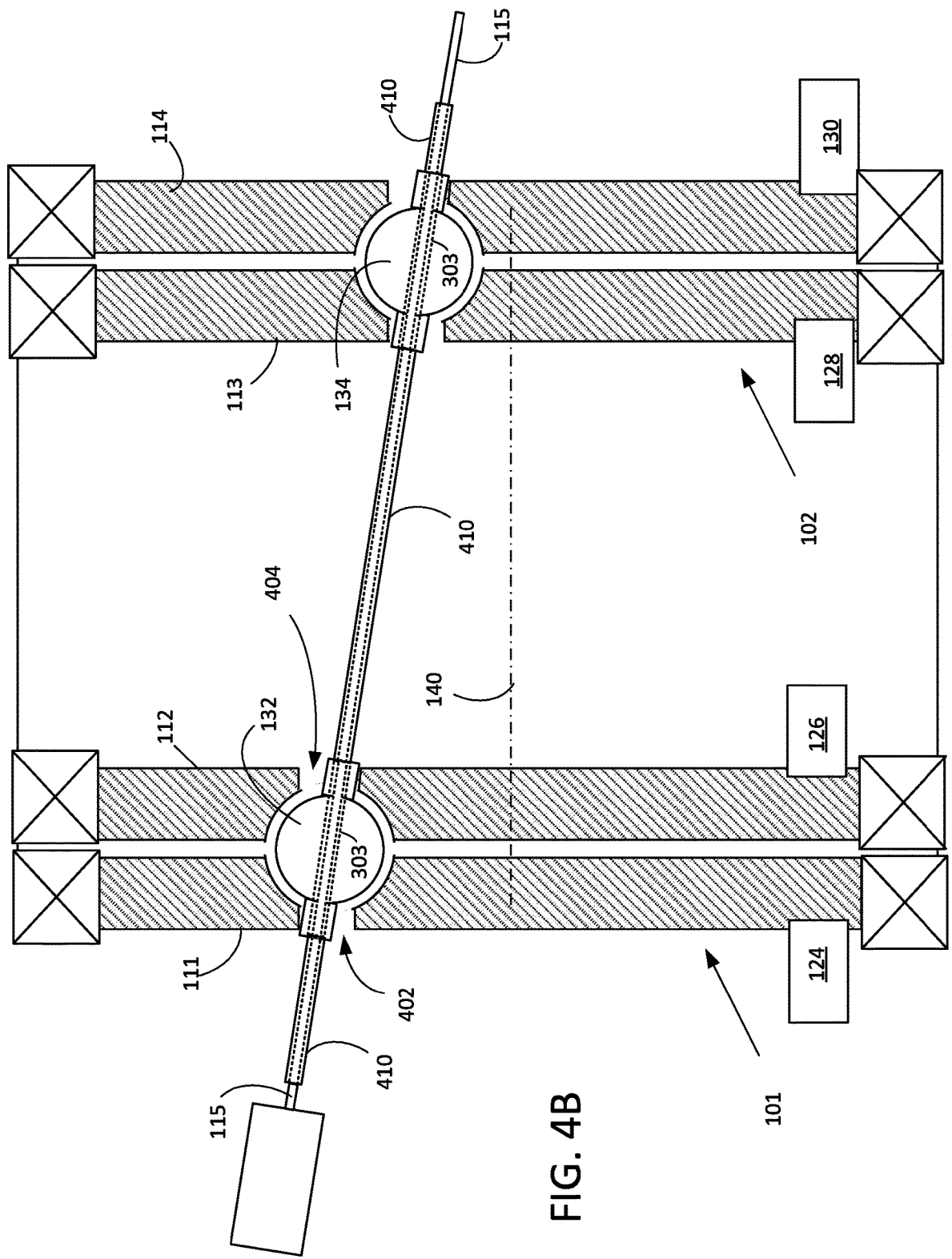

ROBOTIC GUIDE FOR MEDICAL DEVICE

BACKGROUND

Statement of the Technical Field

The present disclosure relates generally to medical guide systems. More particularly, the present disclosure relates to implementing systems and methods which allow a medical device, such as a needle, probe or catheter to be robotically guided for clinical purposes in various types of medical interventions.

Description of the Related Art

In certain types of clinical scenarios a needle or other type of slender elongated medical device (SEMD) must be guided to permit access to subcutaneous tissues and organs. For example, needle guidance can be important when conducting biopsies for sampling of certain tissues. In the absence of careful and precise guidance, the tissue samples obtained during a biopsy may not be entirely satisfactory. Carefully controlled guidance can also be important when using a hypodermic needle to inject a therapeutic substance to a subcutaneous area of a body which is to be treated, when guiding a probe (e.g., a probe for cryoablation), and also when guiding a catheter.

Guidance of an SEMD within a clinical setting is made more complex by the inability to directly view the subcutaneous regions which are the desired target of the SEMD. Moreover, the final position of the SEMD tip is a function of multiple variables including the insertion location, insertion angle and depth of insertion. With so many variables, it is often difficult to ensure that the distal end of the SEMD is correctly positioned for the particular intended clinical purpose.

SUMMARY

Implementing systems and methods are described herein for preventing service disruptions in a computing system. The method involves guiding a slender elongated medical device (such as a needle or a probe) to a target location using a pair of guides. A first position of a first guide is controlled by selectively controlling a relative position of a first pair of transverse guide slots which are respectively defined in a first pair of adjacent control plates. A second position of a second guide is controlled by selectively controlling a relative position of a second pair of transverse guide slots which are respectively defined in a second pair of adjacent control plates. The second pair of adjacent control plates are spaced a predetermined distance from the first pair of adjacent control plates.

An electronic control circuit is used to control the relative movement of each of the first pair of adjacent control plates. The electronic control circuit also controls the relative movement of the second pair of adjacent control plates. The relative movement of the control plates in each mechanism allows the control system to selectively change locations of the first and second guide positions. Consequently, both a lateral displacement of a SEMD axis and an insertion angle of a SEMD alignment axis, as defined by the first and second guides, is robotically controlled. According to one aspect, the required positions of the first and second guides which are necessary for achieving the lateral displacement of the SEMD axis and the insertion angle of the SEMD alignment axis are automatically calculated by the electronic control circuit based at least in part on data specifying an identified target location for a distal end of a needle.

The relative position of the first pair of transverse guide slots is advantageously controlled by selectively rotating each of the first set of adjacent control plates about a respective rotation axis. The respective rotation axis of each of the adjacent control plates can be aligned along a common rotation axis. Similarly, the relative position of the second pair of transverse guide slots can be controlled by selectively rotating each of the second set of adjacent control plates about a respective rotation axis. The relative positions of at least the first set of adjacent control plates can be adjusted by using at least one piezo-electric motor or an electric motor.

In some scenarios, at least one transverse guide slot of the first pair of transverse guide slots can define an arcuate slot guide path. At least one transverse guide slot of the pair of transverse guide slots can also define a linear slot guide path. Also, instead of rotating the control plates, the relative position of the first pair of transverse guide slots can in some scenarios be controlled by laterally displacing a relative position of at least a first one of the first set of adjacent control plates relative to a second one of the first set of adjacent control plates.

The method described herein can be facilitated using a robotic SEMD guide system. The system can include a first and a second guide mechanism which are spaced apart by a predetermined distance. Each guide system includes a pair of adjacent control plates. A first guide slot is defined in a first one of the pair of adjacent control plates and a second guide slot extending transverse to the first guide slot is defined in a second one of the pair of adjacent control plates. A guide is provided which engages both the first and second guide slot. The guide will define a spherical outer bearing surface. Further, the position of the guide is selectively determined responsive to a relative position of the first and second guide slots. An electronic control system is configured to control the guide position in the first and second guide mechanism by selectively varying a relative position of the first and second adjacent control plates. These operations provide robotic control over both a lateral displacement of a SEMD axis and an insertion angle of a SEMD alignment axis, as defined by the first and second guides.

BRIEF DESCRIPTION OF THE DRAWINGS

Embodiments will be described with reference to the following drawing figures, in which like numerals represent like items throughout the figures.

FIG. 1 is a conceptual illustration that is useful for understanding certain features of a robotic guide system for a slender elongated medical device.

FIG. 2 is an exploded view of the robotic guide system in FIG. 1.

FIG. 4B is an enlarged cross-sectional view showing certain features of a robotic guide system.

DETAILED DESCRIPTION

Figure 3:
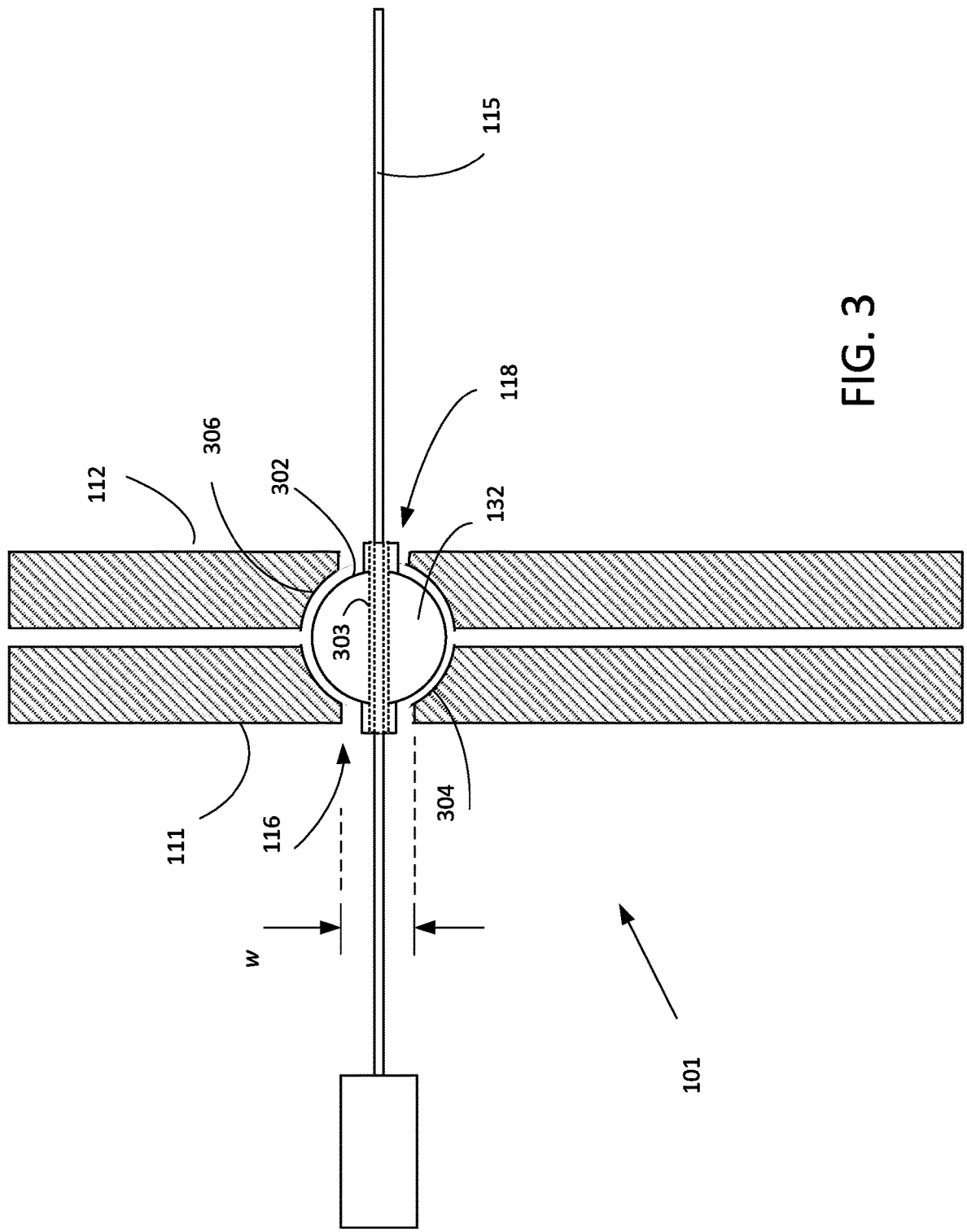
FIG. 3 is an enlarged cross-sectional view of a guide mechanism shown in FIG. 1.

It will be readily understood that the components of the embodiments as generally described herein and illustrated in the appended figures could be arranged and designed in a wide variety of different configurations. Thus, the following more detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout the specification may, but do not necessarily, refer to the same embodiment.

Furthermore, the described features, advantages and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment", "an embodiment", or similar language means that a particular feature, structure, or characteristic described in connection with the indicated embodiment is included in at least one embodiment of the present invention. Thus, the phrases "in one embodiment", "in an embodiment", and similar language throughout this specification may, but do not necessarily, all refer to the same embodiment.

As used in this document, the singular form "a", "an", and "the" include plural references unless the context clearly dictates otherwise. Unless defined otherwise, all technical and scientific terms used herein have the same meanings as commonly understood by one of ordinary skill in the art. As used in this document, the term "comprising" means "including, but not limited to".

To overcome the problem of SEMD guidance in a clinical setting, a targeted SEMD procedure can use a magnetic resonance imaging (MRI) machine, a computed tomography (CT) machine, ultrasound (US) or other imaging modality. These forms of imaging can localize targeted tissues accurately so that the target of the SEMD can be clearly visualized. However, guiding an SEMD to the target is still challenging. To this end, relatively simple SEMD guide devices have been utilized. Simple needle guide templates usually provide a grid of straight needle insertion positions with predetermined intervals, e.g. 5 mm. Robotic devices can provide positioning without intervals and can even support angulated needle insertion to facilitate needle control with 4 Degrees of Freedom (4-DOF). However, such systems are relatively large and complex, which limitations can sometimes prevent prompt clinical implementation. Similar issues arise when attempting to guide other types of slender elongated medical devices percutaneously to specified locations within a patient.

To overcome the limitations of simple templates and conventional robotic guide systems, there is disclosed herein a robotic guide having a compact and simple structure. The robotic guide facilitates 4-DOF control of a Slender Elongated Medical Device (SEMD) by using a paired positioning mechanism. The system offers an angulated insertion guide in a compact form which can be used in a variety of procedures, such as transperineal prostate interventions, percutaneous lung interventions, transcranial brain interventions, and so on. The guide device can be used for guiding a SEMD such as a needle, a probe (e.g., a probe used for cryoablation), or a catheter to a subcutaneous location within a patient that is not readily visible with the naked eye. For convenience, the disclosure herein shall sometimes be provided in the context of a system and method for use in connection with guiding a needle (e.g., a biopsy needle). Still, it should be appreciated that the various guide systems disclosed herein are not limited in this regard and can be used with any other type of SEMD having a similar physical configuration. Accordingly, references to guiding of "needles" should be understood as also including other types of medical devices having similar types of slender elongated configurations including but not limited to biopsy needles, probes, and/or catheters.

Control over the position of an SEMD as described herein is facilitated by an electronic control system. The control system selectively controls a position of a plurality of planar elements by operating one or more motors. Electric motors can be used for this purpose, but the motors are advantageously selected to instead be piezo-electric motors. The piezo-electric motors facilitate a very high degree of precision and accuracy in the SEMD guidance process. Piezo-electric motors are particularly advantageous for use in the guide system since they can be used within an MRI environment where strong magnetic fields adversely affect the operation of ordinary electric motors.

Referring now to FIG. 1, a robotic guide system 100 for an SEMD is comprised of a first and a second guide mechanism 101, 102 which are spaced apart by a predetermined distance d. The exact distance is not critical but the spacing can be selected to facilitate an overall compact arrangement. For example, in some scenarios d can range from between 0.5 cm to 3 cm. In other scenarios, the spacing can be in the range of about 1.0 cm to 2 cm.

As shown in FIG. 1, each guide mechanism is respectively comprised of a pair of adjacent control plates 111, 112 and 113, 114. The control plates are formed of a rigid material such as metal or composite. A first guide slot 116, 117 is defined in each of a first one of the guide plates 111, 113. A second guide slot 118, 119 extends transverse to the first guide slot and is defined in a second of the pair of adjacent control plates 112, 114. FIG. 2 is an exploded view of the robotic guide system 100 which shows that within each guide mechanism, a guide 132, 134 comprises a spherically-shaped outer bearing surface which engages concave inner side walls defining both the first and second guide slot. The concave inner side walls are facing toward each other to create a composite guide channel where the two slots overlap.

A more detailed view of the arrangement is provided in FIG. 3, which shows the guide mechanism 101 in cross-section. As illustrated therein, each guide 132, 134 has a central bore 303 which extends through the guide so that a needle 115 (or other medical device having a similar elongated structure) can be inserted therein. Outer bearing surface 302 of the guide 132 will engage concave inner side walls 304, 306 which partially define the first and second guide slots. As such, a spherical joint is formed whereby the axial alignment of the guide can be varied within the slot. More particularly, the guide 132 will have a guide position which is determined responsive to a relative position of the first and second ones of the first pair of adjacent control plates. For example as control plate 111 is rotated in a first direction 135 and a control plate 112 is rotated in an opposing direction 136, the intersection zone 138 where the two guide slots cross will necessarily vary in position relative to a rotation axis 140. A similar result will occur when control plates 113, 114 are rotated with respect to one another. Notably, guide position control can be obtained by rotating the adjacent control plates in the opposite direction or in the same direction. The guide will be urged by the slots to move along with the point of intersection as between the two transverse slots. Consequently, a position of the guide within each guide mechanism can be selectively varied with a high degree of control. Such control can be highly useful when attempting to guide an SEMD tip 121 to a lesion on a tumor 120.

Figure 4A:
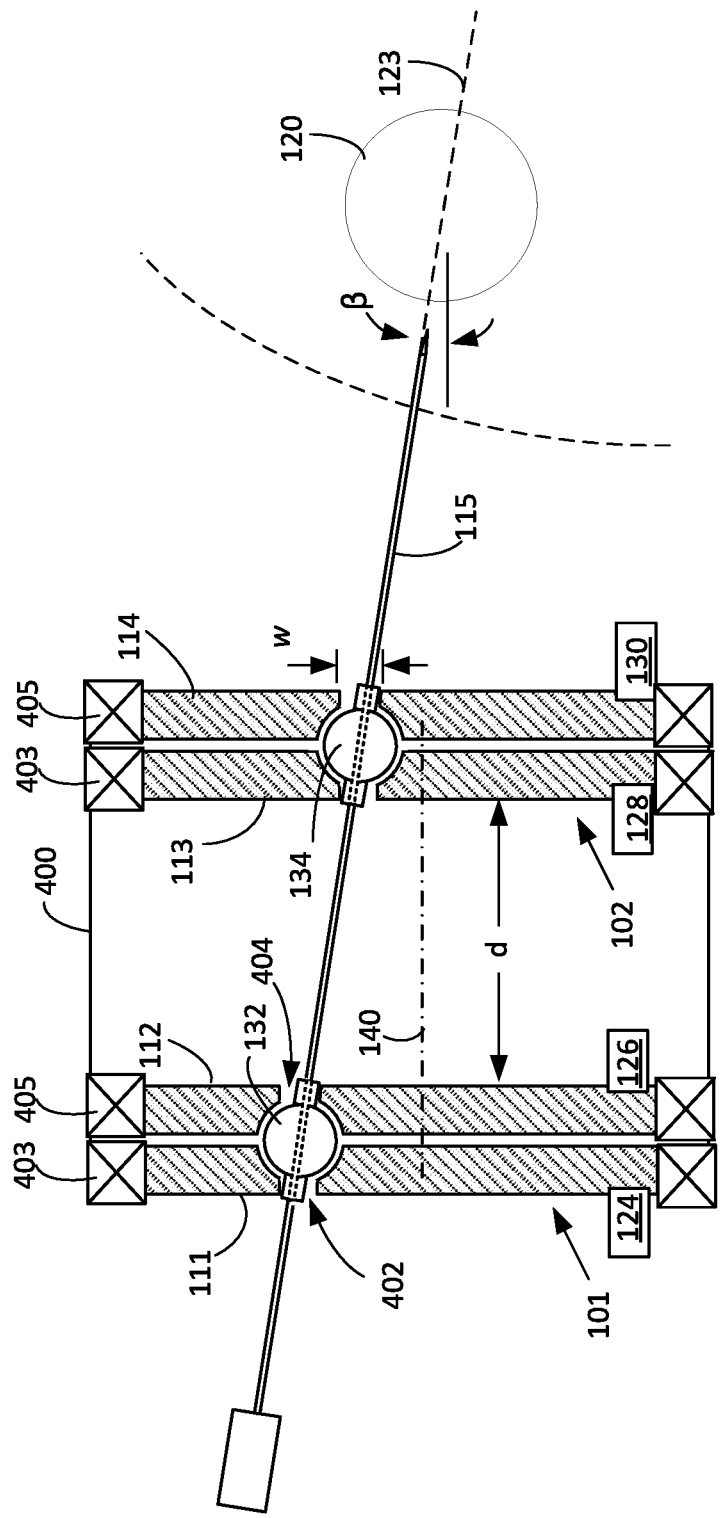
FIG. 4A is a cross-sectional view of a robotic guide system.

Each guide 132, 134 can pivot within a hollow guide space defined at the point where the two slots cross. This pivot motion is facilitated by a clearance space 402, 404 as defined by the slot. To this end, it will be appreciated that guide slots 116, 118, 117, 119 should have a width w that is wide enough to at least facilitate a pivot angle variation β of an alignment axis 123 of am SEMD (such as a needle) as shown in FIGS. 4A and 4B. In such a scenario, the pivot angle β can be defined with respect to the alignment of a rotation axis 140 of the control plates, or with respect to a line orthogonal to the face of the control plates. The exact amount of clearance space required can be determined by the thickness of the control plates and the amount of axis variation of the SEMD that is perceived to be necessary for a particular application. However, the slot width w is advantageously chosen so that it is smaller than the outside diameter of the spherical guide 132 so that the guide is retained within the guide slots.

The first and second guide mechanisms 101, 102 can be controlled independently. Therefore by selectively controlling each of the guide mechanisms 101, 102, a tip 121 of a medical device 115 that is inserted through the central bore in each of the guides 132, 134 can be controlled. For example, as shown in FIG. 1 a transverse or lateral displacement of an SEMD alignment axis 123 in the x, y plane can be controlled. Further, as best understood with reference to FIG. 4, the insertion angle β of a defined by an SEMD alignment axis can be controlled. In this regard it can be observed that the guide 132, 134 can pivot in each of the first and second guide mechanism to accommodate changes in the SEMD alignment axis. A guide system housing or chassis 400 can be used to maintain each of the first and second guide mechanisms in a fixed relationship, spaced apart by a predetermined distance d. The exact distance d is not critical provided that it is sufficient to facilitate angulation of an SEMD as describe herein.

One or more motors 124, 126 can be used to respectively control the relative positions of control plates 111 and 112. Similarly one or more motors 128, 130 can be used to respectively control the relative positions of control plates 113, 114. For example a gear or belt drive linkage (not shown) can be used to facilitate this purpose. In FIGS. 1 and 4A, 4B, one motor is shown for each control plate. However, it is not essential in all scenarios for each control plate to be moved. In some scenarios one control plate 111 could remain stationary while the adjacent control plate 112 is rotated.

In some scenarios, high precision electronic stepper or servo-motors can be used for purposes of moving or rotating the control plates. But in other scenarios (e.g., where the guide system is intended for use within an environment of an MRI machine), the motors can be advantageously selected to comprise piezo-electric motors. A major advantage of the piezoelectric motor in such application is their compatibility with strong magnetic fields that are present within an MRI machine, and the known ability of such piezo-electric motors to control movement in very small increments. If piezo-electric motors are used, a pusher element (not shown) provided in each of the piezo-electric motors can directly engage each of the control plates 111, 112, 113, 114 to urge the necessary movement or rotation thereof. In some scenarios an electronic control circuit can be used to advantageously coordinate the operation of motors 124, 126, 128, 130 in order to guide the tip of an SEMD (e.g. a needle, probe or catheter) to a desired location. In some scenarios, pneumatic or hydraulic actuators can be used in place of piezo-electric motors where use is anticipated within an MRI environment. However, precise control of such actuator elements can be very challenging.

As shown in FIG. 4A, movement of each of the control plates can be facilitated by plate bearings 403, 405. For example, such plate bearings can facilitate rotation of each of the control plates about rotation axis 140. The control plates can have a circular outer periphery and the plate bearings 403, 405 can be arranged to facilitate rotation of each plate about the central rotation axis 140.

In the system shown in FIG. 4A, 4B, a sterile field can be maintained by using a thin, rigid or semi-rigid, sterile, plastic sheath (tube) around the SEMD during a procedure. Such an arrangement is best understood with reference to FIG. 4B, which shows an enlarged view of the robotic guide system, with a disposable sheath 410 in place over the SEMD 115. The disposable sheath extends along at least a portion of a length of the SEMD 115 where it traverses through the central bore 303 of each guide 132, 134. The arrangement prevents physical contact between the SEMD 115 and the side walls defining the central bore 303. It would be difficult, if not impossible, to autoclave the robotic guide system in its entirety. The sheath 410 solves the problem of maintaining a sterile site and ensures the that the SEMD 115 remains sterile. The sheath can be formed of any suitable low density inert, non-toxic material such as nylon, polyester, polyimide, polyethylene or Polyether Block Amide.

Figure 5:
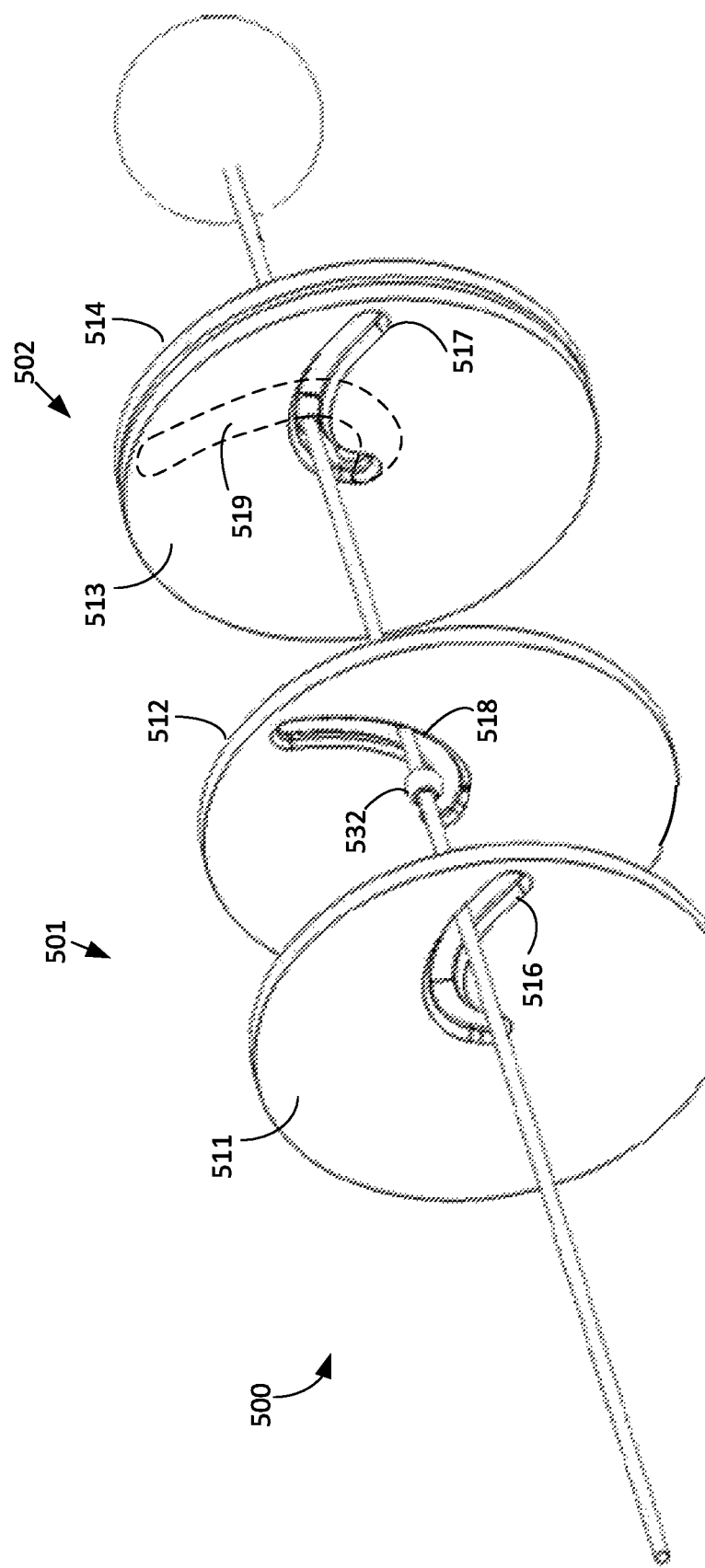
FIG. 5 is a partially exploded view of a robotic guide system in which a plurality of curved guide slots are utilized.

In FIGS. 1 and 2, one of the guide slots 116, 117 is shown as extending linearly across the surface of each control plate and a second guide slot 118, 119 is curved. However in some scenarios it can be advantageous to form the guide slots in adjacent plates so that they both extend in a curved or arcuate path across the surface of one or more of the plates. Such an arrangement can be useful for reducing friction or binding as between the bearing surfaces of the guide and concave inner side walls that form each guide slot. An SEMD guide system 500 shown in FIG. 5 has a plurality of curved or arcuate guide slots 516, 518, 517, 519 disposed respectively in control plates 511, 512, 513, and 514.

In some scenarios, a guide slot 516 can be a mirror image of a guide slot 518. Since the positioning is achieved by mechanical constraints of the two slots on rotating disks, the intersection angle of the two slots should be substantially perpendicular. As such, a planar positioning of the guide can be described as a function of angular position of the two disks on a cylindrical coordinate, which can be described as follows:

$$x = e^t \cos(t) - 1 \quad y = e^t \sin(t) \quad (1)$$

Where, x and y are the spatial coordinate, and t is a parametric variable which relates x, y and the radius of the disk. Inverse kinematically, angular position of the disk can be determined:

$$\theta_{disk_1}, \theta_{disk_2} = \arctan\left(\frac{y}{\gamma}\right) \pm \left|\theta_{home} - \ln[(x^2 + y^2)^{1/2}]\right| \quad (2)$$

Figure 6:
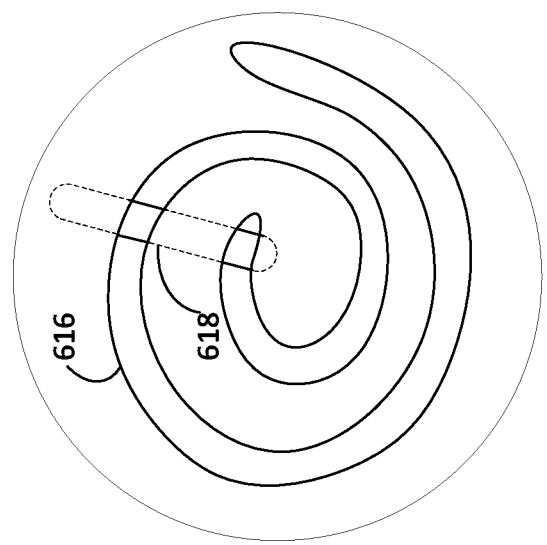
FIG. 6 is a schematic representation of a pair of adjacent control plates showing a first plate with a curved or spiral guide slot and a second plate with a linear guide slot.

Where, $\theta_{disk_1}$ and $\theta_{disk_2}$ and $\theta_{home}$ are angular positions of the disks and their home position, respectively. By connecting the intersecting SEMD guide positions on the two double disk guide mechanisms, a 4-DOF manipulation can be obtained. FIG. 4A illustrates the guide concept showing angulated SEMD insertion. Once a target location and insertion angle are identified, both guide slot intersecting positions on each disk set can be obtained. Then, a required angular position of each disk can be computed. Of course, other slot arrangements are also possible, including combinations of linear and spiral-curved slots 616, 618 as shown in FIG. 6.

Figure 7:
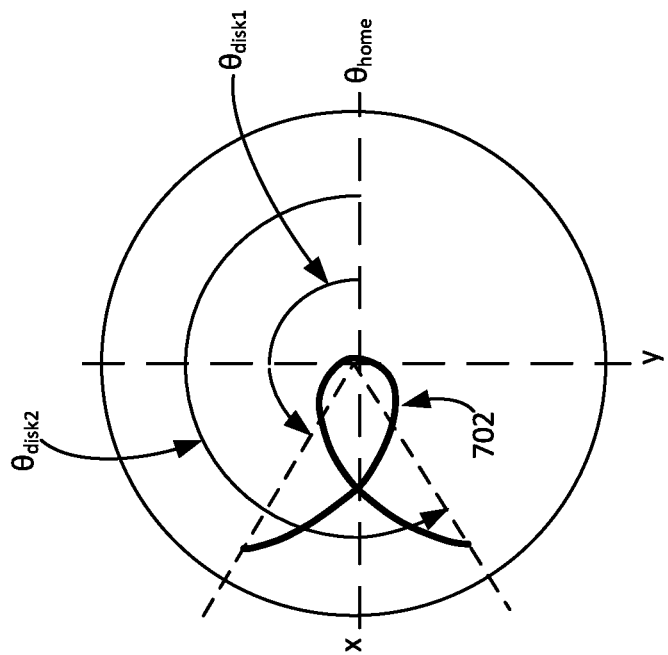
FIG. 7 is a schematic diagram of a 2-DOF guidance mechanism comprised of two control plates and showing a plot of an intersecting point of two curvatures for providing planar disk positioning.

Turning now to FIG. 7, there is shown a graph that is useful for understanding how an x, y coordinate position of a guide 532 can move in the x, y plane as control plates 511, 512 are moved. The graph shown in FIG. 7 shows a path 702 that a guide 532 would travel as the control plates 511 and 523 are rotated respectively through angles $\theta_{disk_1}$ and $\theta_{disk_2}$. Relative to a starting point defined as $\theta_{home}$. As can be observed in FIG. 7, the guide will follow an arcuate path in the x, y plane which is determined by the shape of the slots and the rotation of the plates.

Figure 8:
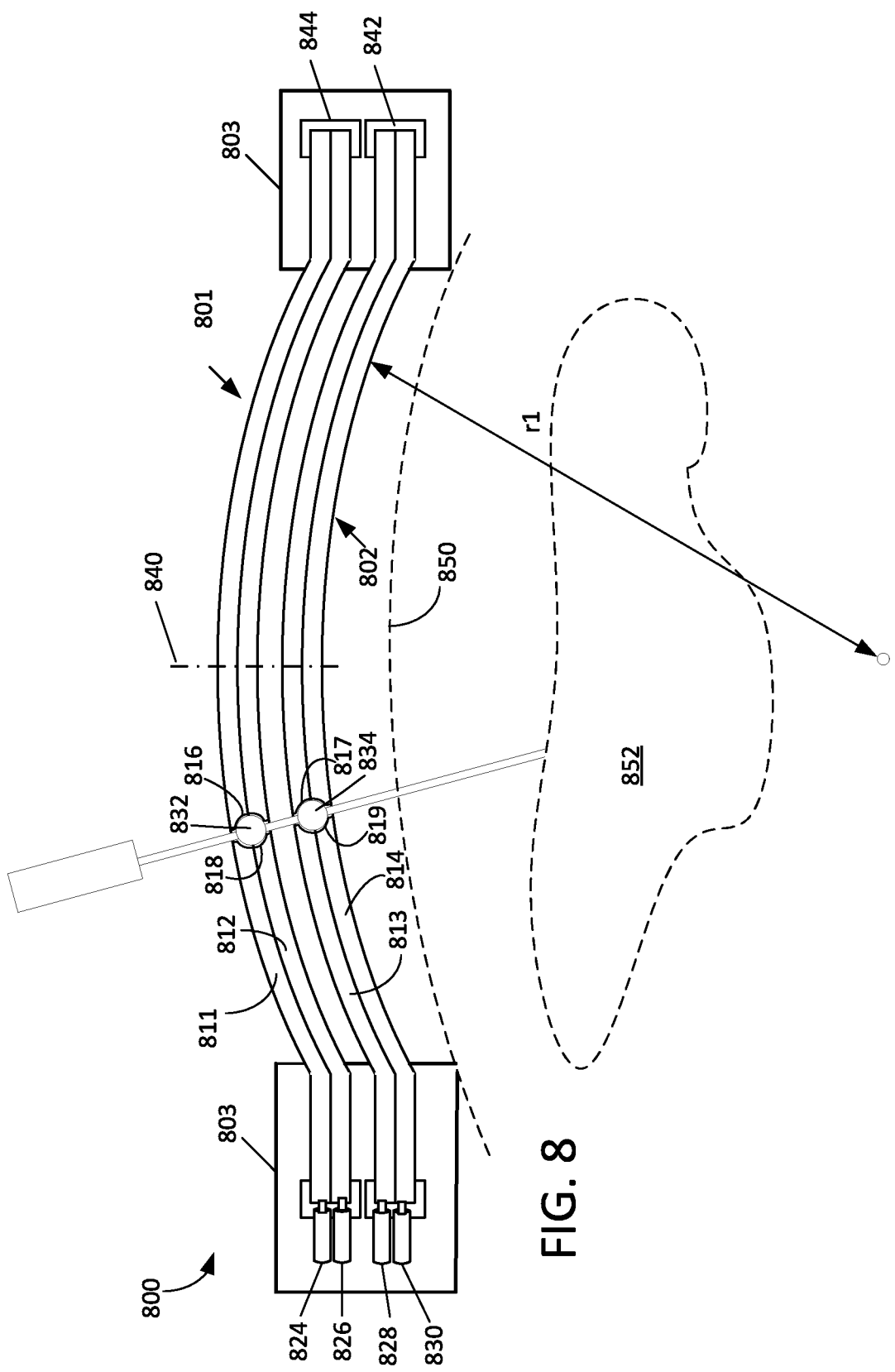
FIG. 8 is a diagram that is useful for understanding a robotic guide system in which the control plates have a concave profile with a relatively large radius of curvature.

The control plates referenced herein can be planar as shown in FIGS. 1-5. Such an arrangement can be suitable for conducting biopsies of certain smaller organs. For example, the arrangement shown in FIGS. 1-5 can work well for biopsies the prostate gland which are performed through the perineum. But in other scenarios it can be advantageous for the control plates to have a concave shape with a radius of curvature r1. Such an arrangement is shown in robotic guide system 800 of FIG. 8. The curvature defined by r1 can be advantageous in some scenarios so as to avoid skin contact where the skin itself is not flat. As illustrated therein, the guide system 800 can be rested upon the non-flat skin 850 of a subject for performing percutaneous procedures such as biopsies and ablations. The slightly concave arrangement can be particularly useful for scenarios involving the lungs, liver and other larger organs 852.

In other respects, the robotic guide system 800 can be of a similar arrangement to that which has been described in FIGS. 1-5. Thus, the system can include a first and a second guide mechanism 801, 802 which are spaced apart by a predetermined distance. Each guide mechanism 801, 802 can be respectively comprised of a pair of adjacent control plates 811, 812 and 813, 814. The control plates can have a concave shape as show. A first guide slot 816, 817 is defined in each of a first one of the control plates 811, 813. A second guide slot 818, 819 extends transverse to the first guide slot and is defined in each of a second one of the control plates 812, 814. A guide 832, 834 comprises a spherical outer bearing surface which engage side walls defining both the first and second guide slot.

Figure 9:
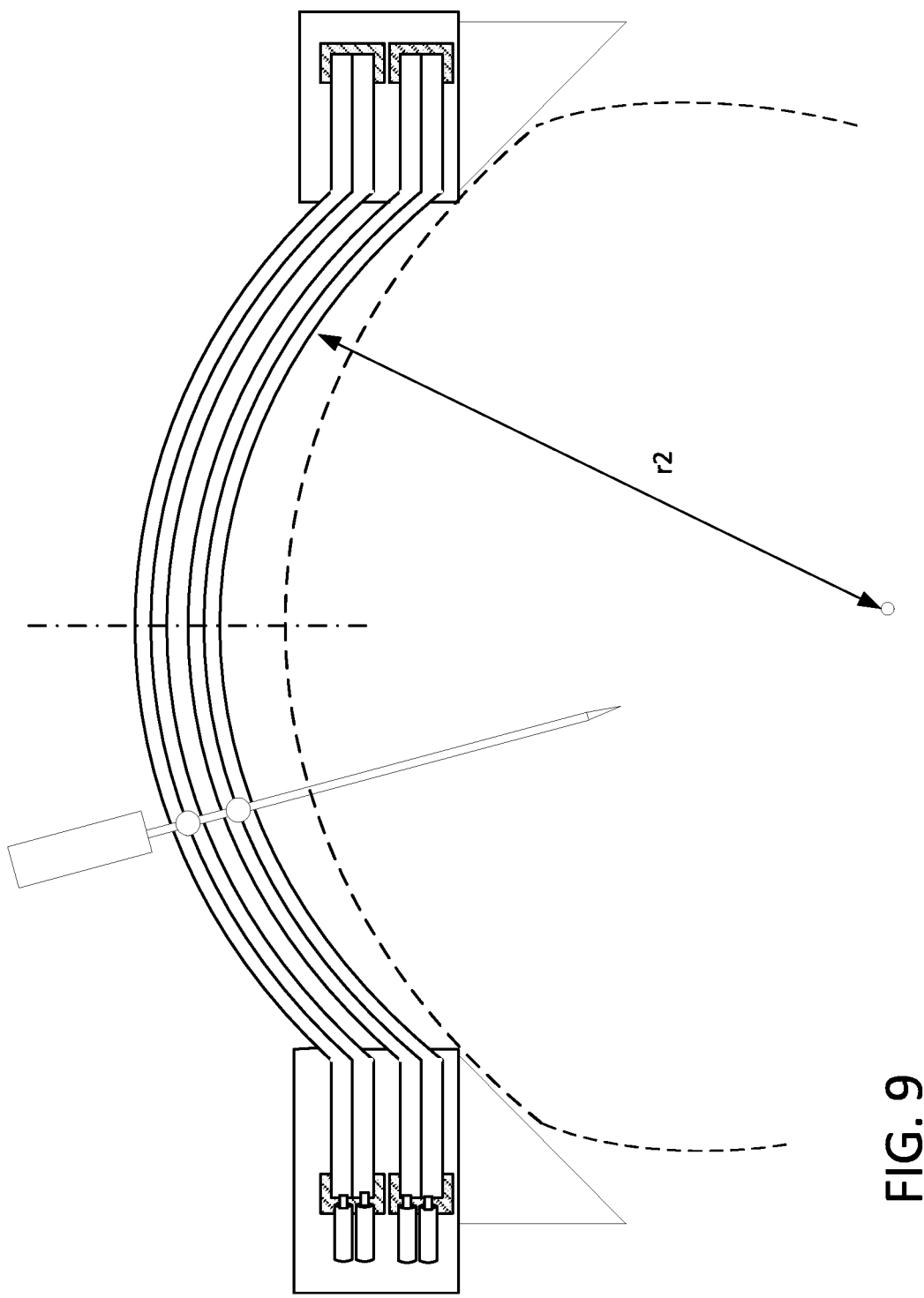
FIG. 9 is a diagram that is useful for understanding a robotic guide system in which the control plates have a concave profile with a relatively small radius of curvature.

Plate bearings 842, 844 can support the plates to facilitate relative movement thereof. For example, in some scenarios the control plates can have a circular outer periphery and the plate bearings 842, 844 can be arranged to facilitate rotation of each plate about a central rotation axis 840. A plurality of motors 824, 826, 828, 830 can be used to provide relative movement of the control plates as needed. As shown in FIG. 9, a similar arrangement with a different radius of curvature r2 can be used for cranial applications of the guide system.

Figure 10A:
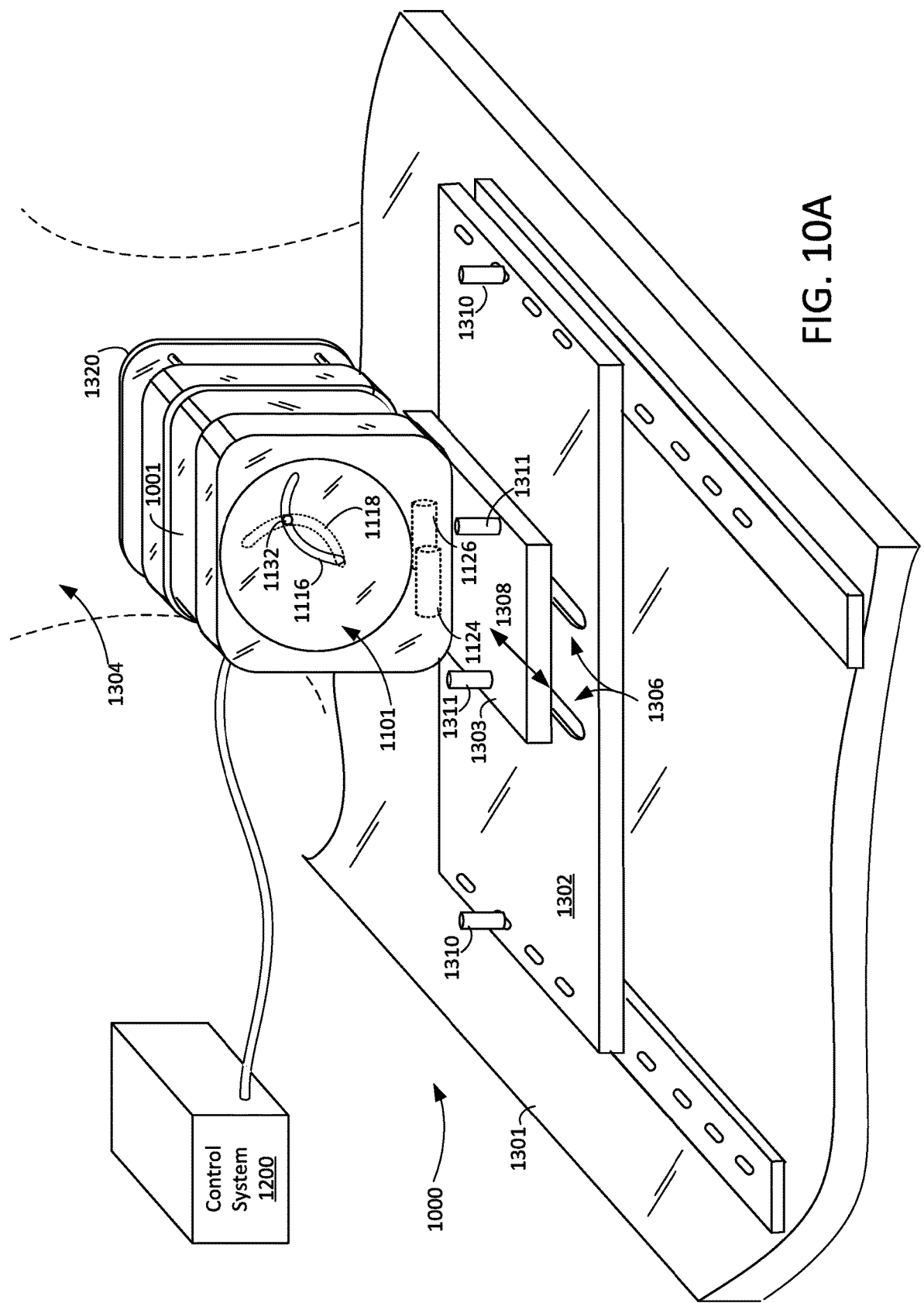
FIG. 10A is a diagram that is useful for understanding a prostate intervention setup using a 4-DOF guide system as described herein.
Figure 10B:
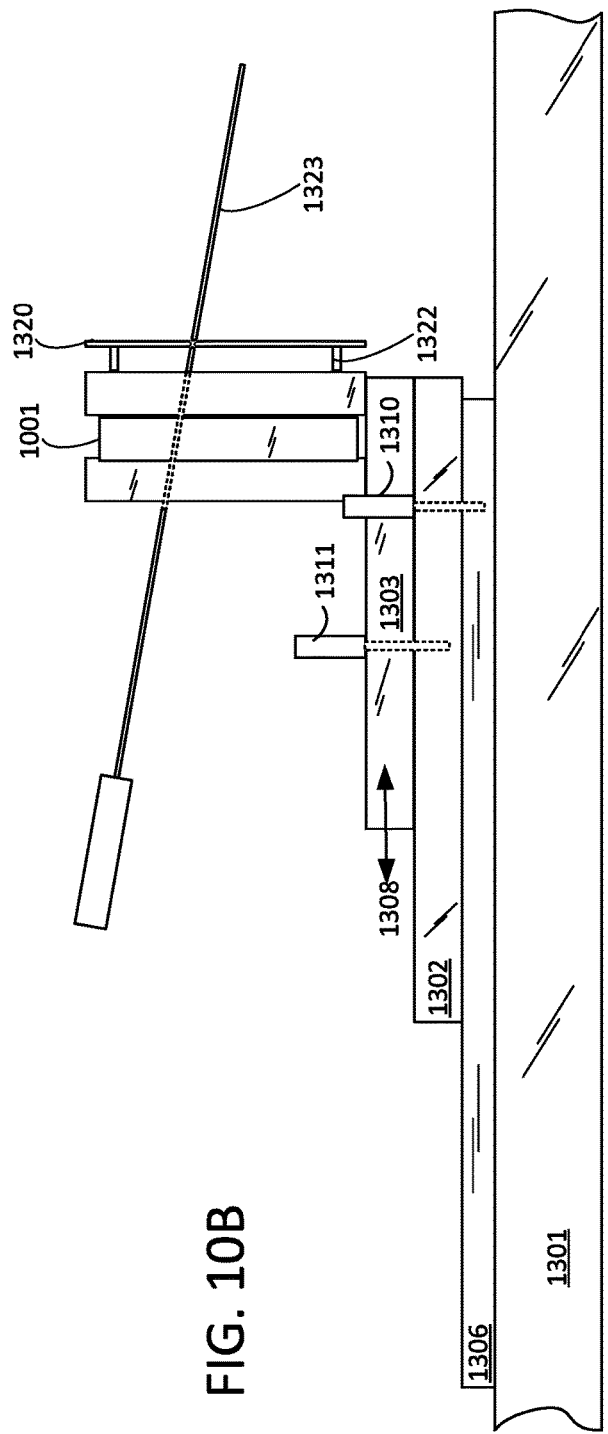
FIG. 10B is a side view of the prostate intervention setup in FIG. 10A.

FIGS. 10A and 10B are useful for understanding how a guide system 1000 can be used for MRI-guided prostate intervention. The guide system 1000 has an arrangement similar to the guide systems described in FIGS. 1-7. As such, the guide system 1000 includes a plurality of guide mechanisms 1101 disposed in a housing 1001 and spaced apart by a predetermined distance. Each of the guide mechanisms is comprised of a pair of adjacent rotating control plates similar to that described herein with respect to FIGS. 1-4. The control plates in each guide mechanism have transversely opposed guide slots 1116, 1118. Each of the guide mechanisms can support and control a position of a guide 1132. A control system 1200 can control the operation of a plurality of motors 1124, 1126 for determining a position of the guide.

Figure 11:
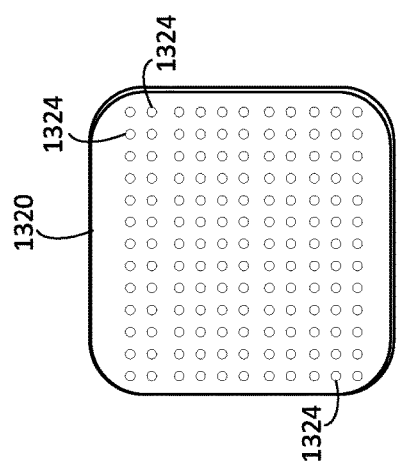
FIG. 11 is a drawing that is useful for understanding a perforated contact plate.

The guide system can be mounted on a platen 1302 which can be fixed on a patient table 1301 using a locking element such as posts 1310. The housing 1001 of the guide system can be placed against a perineal surface 1304 of a patient by moving a base plate 1303 of the guide system in directions indicated by arrow 1308 along tracks 1306. As shown in FIG. 11, a detachable skin contact plate 1320 is gently pushed against the perineum to stabilize skin during needle insertions. As shown in FIG. 11 the contact plate can have a multiplicity of apertures 1324 disposed through which a needle is guided. The detachable skin contact plate also allows the guide robot to be non-sterile except for the skin contact plate. In some scenarios, the intervention site can be maintained in a sterile condition by positioning a sterile plastic sheet on the patient and another on the skin contact plate. This will maintain sterility of the biopsy/intervention site. Once the guide housing 1001 is properly positioned, the base plate 1303 can be secured in position using suitable hardware such as posts 1311 which are inserted into alignment apertures (not shown) disposed within the platen 1302. Thereafter, a medical device, such as an SEMD 1323, can be inserted into the guides 1132 in a manner similar to that described herein with respect to FIG. 4. As shown in FIG. 10B, the robotic guide system can direct the SEMD through one of the selected apertures 1324.

Figure 12:
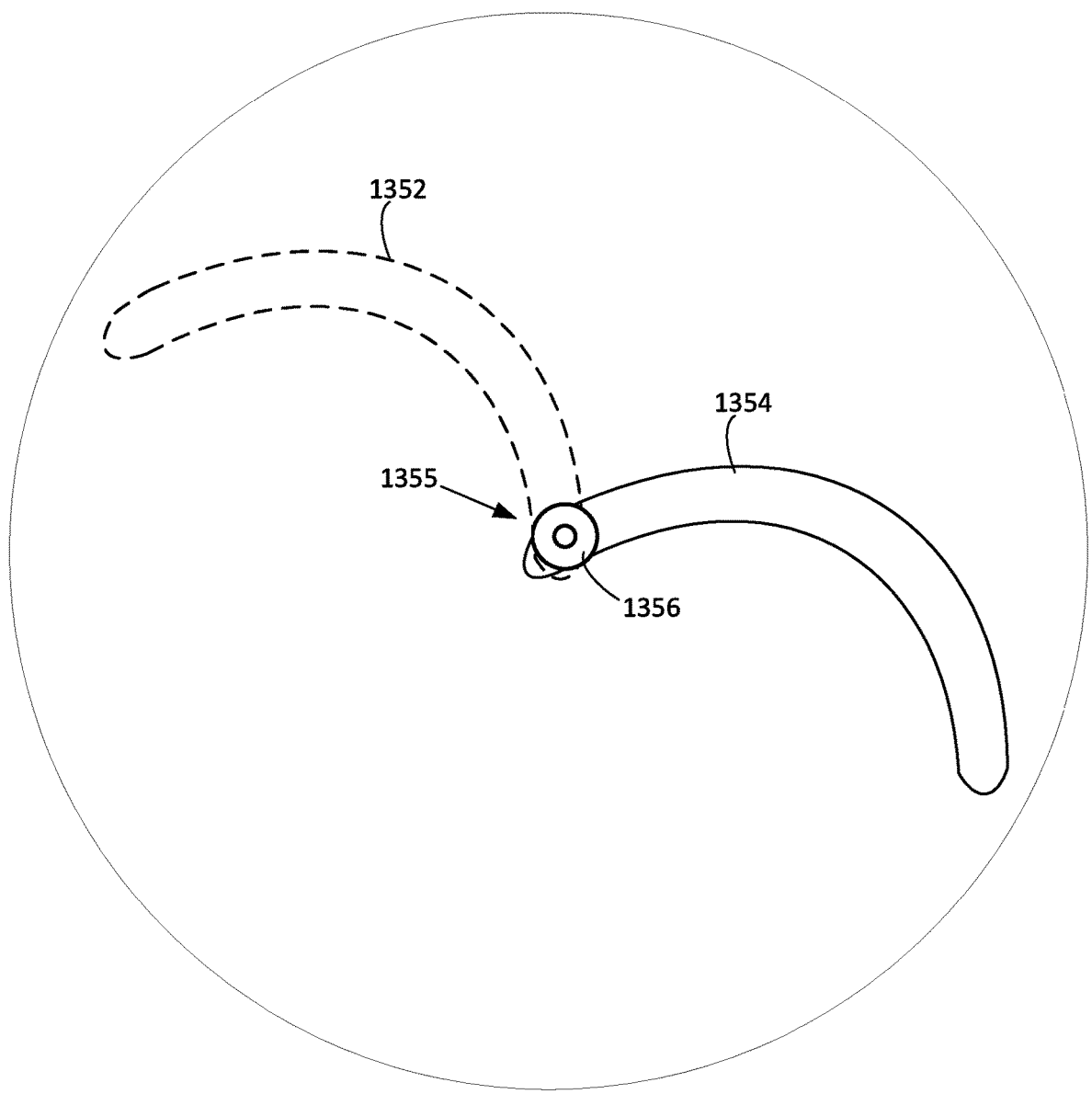
FIG. 12 is a drawing that is useful for understanding an guide problem that can arise when an SEMD guide is aligned with a rotation axis of the control plates.
Figure 13:
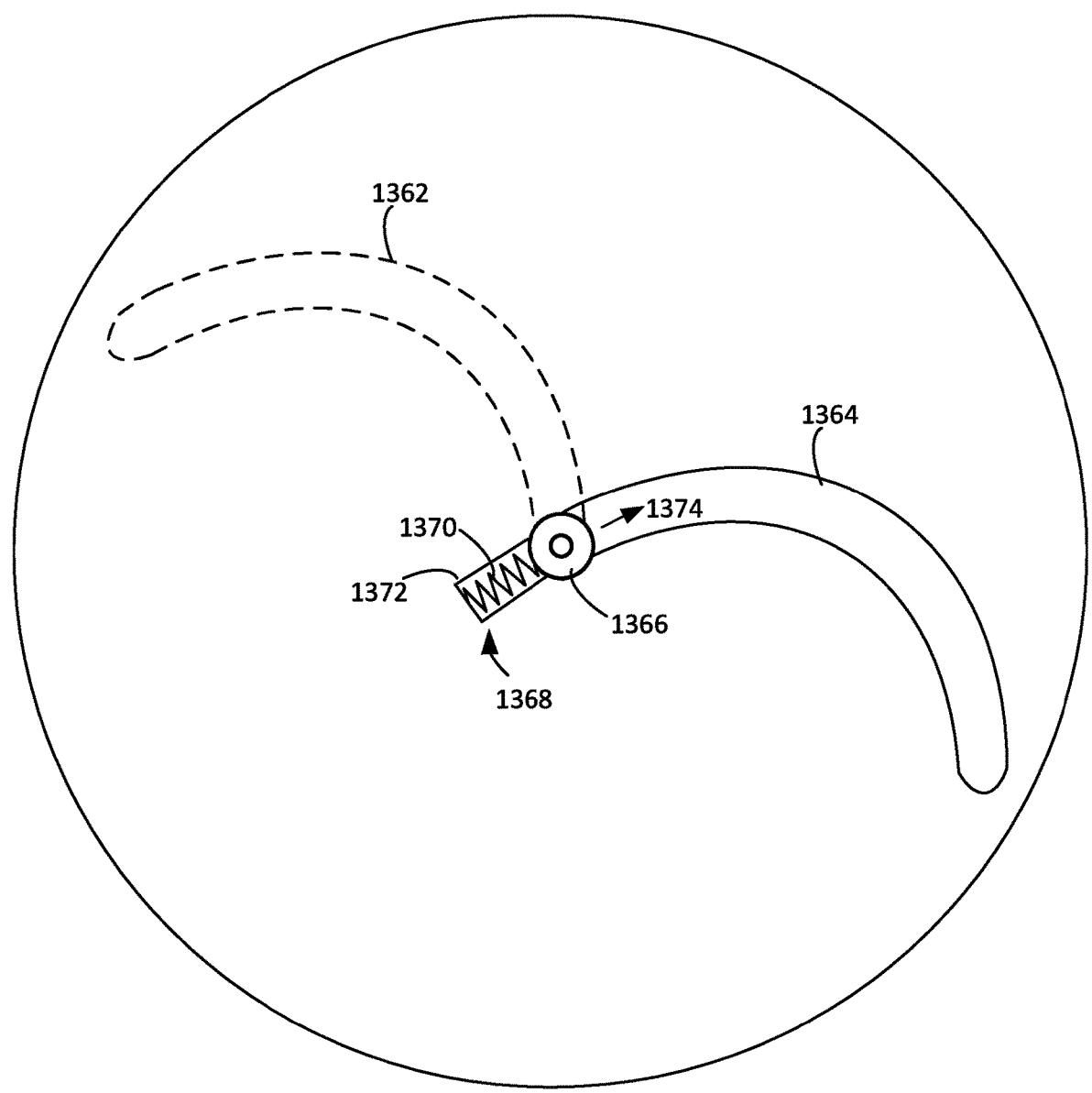
FIG. 13 is a drawing that is useful for understanding how the problem described in FIG. 12 can be solved with a resilient biasing member.
Figure 14:
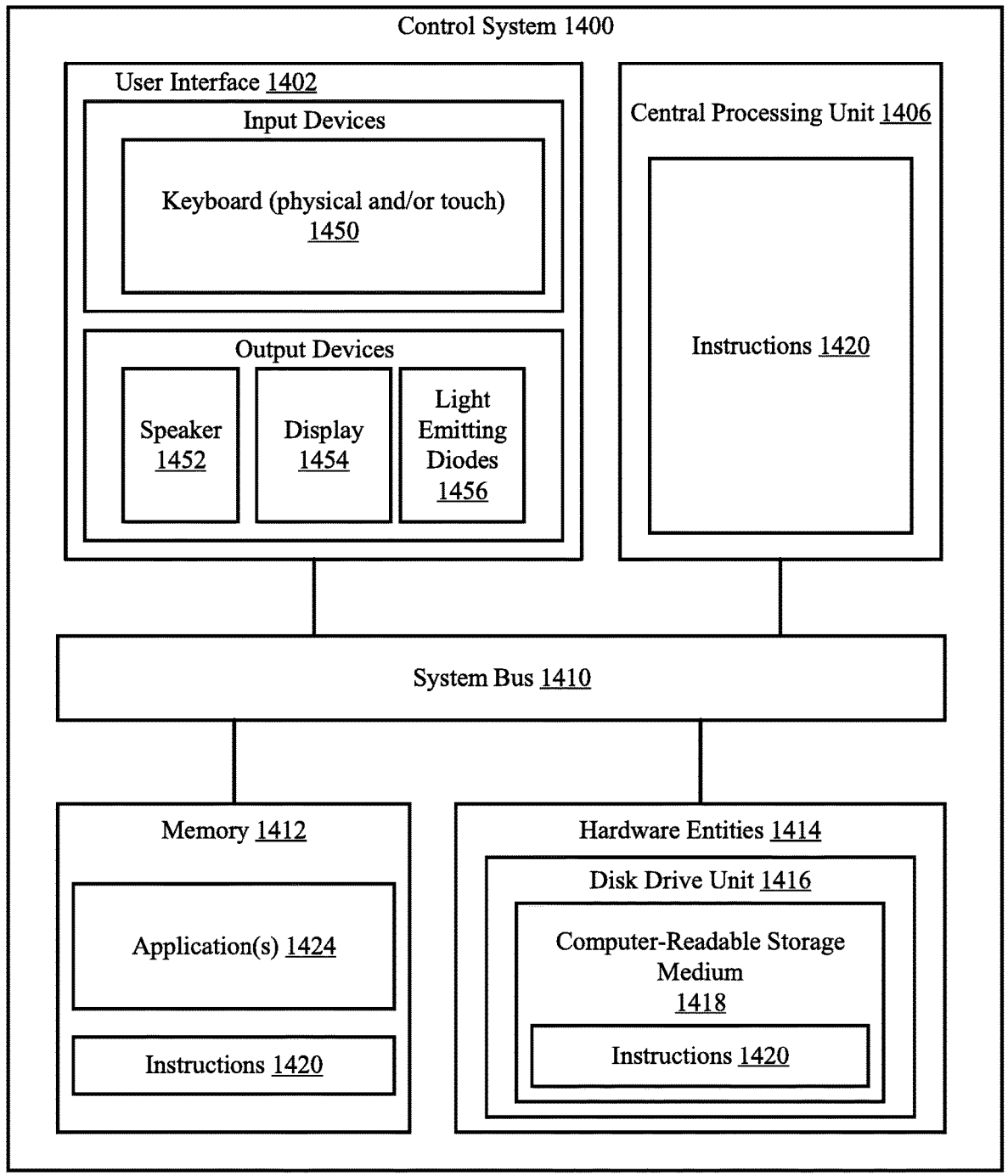
FIG. 14 is a block diagram that is useful for understanding an example architecture of a control system which can be used to control the guide system.

In some scenarios disclosed herein, the two transverse guide slots will advantageously terminate at a location approximately aligned with a rotation axis of the two adjacent control plates. For example, such rotation axis can be aligned with a center of each adjacent plate. Such a scenario is shown in FIG. 12 where two curved guide slots 1352, 1354 each have one end aligned with a central axis of rotation 1355. But a problem can arise when the SEMD guide 1356 is actually urged to this central axis position by the operation of the transverse guide slots. The SEMD guide 1356 may become lodged in this location and unable to move. This problem is alleviated by adding a push mechanism at an end portion of one of the transverse slots that is aligned with the center axis. Such an arrangement is shown in FIG. 13 which shows that a push mechanism 1368 can comprise a biasing member, such as a spring 1370, which is retained within a spring retainer space 1372. The biasing member provides a resilient bias force which advantageously urges the SEMD guide in a direction 1374, away from the central axis of rotation. This biasing force is useful because it prevents the SEMD guide 1366 from becoming lodged at this central axis location during guiding operations. Referring now to FIG. 14, there is provided an illustration of an exemplary control system 1400 which can be used for controlling a guide system as described herein. The control system can include, but is not limited to, machines (or computing devices) running a Windows OS (e.g., a personal computer or server). Such machines (or computing devices) are well known in the art, and will not be described in detail herein. Still, it should be understood that such machines are modified to implement all or a portion of the methods described herein. Such modifications can include software modifications, hardware modification or a combination of both.

Control system 1400 may include more or less components than those shown in FIG. 14. However, the components shown are sufficient to disclose an illustrative embodiment implementing the present solution. The hardware architecture of FIG. 14 represents one embodiment of a representative control system or computing device configured to facilitate the SEMD guidance control operations described herein.

Some or all the components of the control system 1400 can be implemented as hardware, software and/or a combination of hardware and software. The hardware includes, but is not limited to, one or more electronic circuits. The electronic circuits can include, but are not limited to, passive components (e.g., resistors and capacitors) and/or active components (e.g., amplifiers and/or microprocessors). The passive and/or active components can be adapted to, arranged to and/or programmed to perform one or more of the methodologies, procedures, or functions described herein.

As shown in FIG. 14, the control system 1400 comprises a user interface 1402, a Central Processing Unit ("CPU") 1406, a system bus 1410, a memory 1412 connected to and accessible by other portions of computing device 1400 through system bus 1410, and hardware entities 1414 connected to system bus 1410. The user interface can include input devices and output devices, which facilitate user-software interactions for controlling operations of the computing device 1400. The input devices include, but are not limited, a physical and/or touch keyboard 1450. The input devices can be connected to the computing device 1400 via a wired or wireless connection (e.g., a Bluetooth® connection). The output devices include, but are not limited to, a speaker 1452, a display 1454, and/or light emitting diodes 1456.

At least some of the hardware entities 1414 perform actions involving access to and use of memory 1412, which can be a Random Access Memory ("RAM"), a disk drive and/or a Compact Disc Read Only Memory ("CD-ROM"). Hardware entities 1414 can include a disk drive unit 1416 comprising a computer-readable storage medium 1418 on which is stored one or more sets of instructions 1420 (e.g., software code) configured to implement one or more of the methodologies, procedures, or functions described herein. The instructions 1420 can also reside, completely or at least partially, within the memory 1412 and/or within the CPU 1406 during execution thereof by the computing device 1400. The memory 1412 and the CPU 1406 also can constitute machine-readable media. The term "machine-readable media", as used here, refers to a single medium or multiple media (e.g., a centralized or distributed database, and/or associated caches and servers) that store the one or more sets of instructions 1420. The term "machine-readable media", as used here, also refers to any medium that is capable of storing, encoding or carrying a set of instructions 1420 for execution by the control system 1400 and that cause the control system 1400 to perform any one or more of the methodologies of the present disclosure.

In some scenarios, the hardware entities 1414 include an electronic circuit (e.g., a processor) programmed for facilitating control over the position of a plurality of movable control plates to guide an SEMD, toward an intended target. In this regard, it should be understood that the electronic circuit can access and run application(s) 1424 installed on the computing device 1400. The functions of the software application(s) 1424 are apparent from the following discussion of the present solution. For example, the software application is configured to perform one or more of the operations described below in relation to FIGS. 1-13.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application. Thus, the breadth and scope of the present invention should not be limited by any of the above-described embodiments. Rather, the scope of the invention should be defined in accordance with the following claims and their equivalents.

What is claimed is:

1. A method for guiding a slender elongated medical device (SEMD) to a target location in a clinical setting, comprising:

controlling a first guide position of a first guide by selectively controlling a position of a first guide slot defined in a first control plate with respect to a position of a second guide slot defined in a second control plate, selecting a first path of the first guide slot to extend in a direction transverse to a second path of the second guide slot so that the first guide slot and second guide slot together define a first pair of transverse guide slots which cross at the first guide position, and positioning the first control plate adjacent to the second control plate so that the first and second control plate together define a first pair of adjacent control plates;

controlling a second guide position of a second guide by selectively controlling a position of a third guide slot defined in a third control plate with respect to a position of a fourth guide slot defined in a fourth control plate, selecting a third path of the third guide slot to extend in a direction transverse to a fourth path of the fourth guide slot so that the third guide slot and the fourth guide slot together define a second pair of transverse guide slots which cross at the second guide position, and positioning the third control plate adjacent to the fourth control plate so that the third and fourth control plates together define a second pair of adjacent control plates, the second pair of adjacent control plates spaced a predetermined distance from the first pair of adjacent control plates;

using an electronic control circuit to move at least one of the first pair of adjacent control plates and at least one of the second pair of adjacent control plates so as to selectively change locations of the first and second guide positions, whereby both a lateral displacement of an SEMD axis and an insertion angle of an SEMD alignment axis, as defined by the first and second guides, is robotically controlled.

2. The method according to claim 1, wherein the position of the first guide slot is controlled with respect to the position of the second guide slot by selectively rotating at least one of the first control plate and the second control plate about a respective rotation axis.

3. The method according to claim 2, wherein the respective rotation axis of each of the first and second control plates is aligned along a common rotation axis.

4. The method according to claim 2, wherein the position of the third guide slot is controlled with respect to the position of the fourth guide slot by selectively rotating at least one of the third and fourth control plate about a respective rotation axis.

5. The method according to claim 1, further comprising changing the relative position of the first control plate with respect to the second control plate using at least one piezo-electric motor.

6. The method according to claim 1, further comprising selecting at least one of the first path and the second path to define an arcuate path.

7. The method according to claim 1, further comprising selecting at least one of the first path and the second path to define a linear path.

8. The method according to claim 1, wherein the position of the first guide slot is controlled with respect to the second guide slot by laterally displacing a position of at least the first control plate with respect to the second control plate.

9. The method according to claim 1, wherein the first guide position and the second guide position necessary for achieving the lateral displacement of the SEMD alignment axis and the insertion angle of the SEMD alignment axis are automatically determined by the electronic control circuit based at least in part on data specifying an identified target location for a distal end of the SEMD.

10. The method according to claim 1, further comprising urging at least the first guide to the first guide position by engaging an outer bearing surface defined by the first guide with first inner side walls defining the first guide slot and second inner side walls defining the second guide slot.

11. A robotic guide system for a Slender Elongated Medical Device (SEMD), comprising:
a first and a second guide mechanism which are spaced apart by a predetermined distance, each comprising
a pair of adjacent control plates including a first control plate and a second control plate;
a first guide slot defined in the first control plate and a second guide slot defined in the second control plate, the second guide slot extending along a second path transverse to a first path defined by the first guide slot; and
a guide which is configured to engage both the first and second guide slot, the guide having a guide position determined by a position of the first control plate relative to a position of the second control plate; and
an electronic control system configured to control the guide position respectively in each of the first and second guide mechanism by selectively varying the position of the first control plate relative to the position of the second control plate, whereby both a lateral displacement of an alignment axis of the SEMD and an insertion angle of the alignment axis with respect to a target are robotically controlled using the guide that is provided in each of the first and second guide mechanism.

12. The robotic guide system according to claim 11, wherein the guide provided in each of the first and second guide mechanism has a ball shape which facilitates angular displacement of the alignment axis as the guide is moved within the first guide slot and the second guide slot.

13. The robotic guide system according to claim 11, wherein each of the first and second guide mechanisms is configured so that a relative position of the first guide slot with respect to the second guide slot is controlled by selectively rotating about a rotation axis at least the first control plate.

14. The robotic guide system according to claim 13, wherein in each of the first and second guide mechanism, the second control plate is also configured to rotate abou the rotation axis.

15. The robotic guide system according to claim 13, wherein the rotation axis in the first guide mechanism is axially aligned with the rotation axis in the second guide mechanism.

16. The robotic guide system according to claim 11, wherein each of the first and second guide mechanism includes at least one piezo-electric motor which is configured to change the position of the first control plate relative to the position of the second control plate responsive to the electronic control system.

17. The robotic guide system according to claim 11, wherein in each of the first and second guide mechanism, at least one of the first and second guide slots define an arcuate guide path.

18. The robotic guide system according to claim 11, wherein in each of the first and second guide mechanism, at least one of the first and second guide slots defines a linear guide path.

19. The robotic guide system according to claim 11, wherein at least one of the first and second guide mechanism is configured so that a position of the first guide slot relative to a position of the second guide slot is controlled by laterally displacing the position of the first control plate relative to the position of the second control plate.

20. The robotic guide system according to claim 11, wherein the control system is configured to automatically determine the guide position in the first guide mechanism and the guide position in the second guide mechanism which are necessary for achieving the lateral displacement of the alignment axis and the insertion angle, and wherein each of the guide positions are determined at least in part on data specifying an identified target location for a distal end of the SEMD.

* * * * *